(12) United States Patent
Audia et al.

(10) Patent No.: US 11,612,615 B2
(45) Date of Patent: Mar. 28, 2023

(54) COMBINED ADMINISTRATION OF CYSTEINE-ASPARTIC PROTEASE INHIBITORS WITH P2Y12 RECEPTOR ANTAGONISTS PROTECTS THE HEART AGAINST MYOCARDIAL INFARCTION

(71) Applicants: Jonathon P. Audia, Mobile, AL (US); James M. Downey, Mobile, AL (US); Diego Alvarez, Mobile, AL (US); Michael V. Cohen, Mobile, AL (US)

(72) Inventors: Jonathon P. Audia, Mobile, AL (US); James M. Downey, Mobile, AL (US); Diego Alvarez, Mobile, AL (US); Michael V. Cohen, Mobile, AL (US)

(73) Assignee: The University of South Alabama, Mobile, AL (US)

( * ) Notice: Subject to any disclaimer, the term of this patent is extended or adjusted under 35 U.S.C. 154(b) by 0 days.

(21) Appl. No.: 16/608,262

(22) PCT Filed: Apr. 27, 2018

(86) PCT No.: PCT/US2018/029801
§ 371 (c)(1),
(2) Date: Oct. 25, 2019

(87) PCT Pub. No.: WO2018/200958
PCT Pub. Date: Nov. 1, 2018

(65) Prior Publication Data
US 2021/0100827 A1 Apr. 8, 2021

Related U.S. Application Data

(60) Provisional application No. 62/602,546, filed on Apr. 27, 2017.

(51) Int. Cl.
| A61K 31/7076 | (2006.01) |
| A61P 9/10 | (2006.01) |
| A61K 31/519 | (2006.01) |
| A61K 38/55 | (2006.01) |

(52) U.S. Cl.
CPC ........ *A61K 31/7076* (2013.01); *A61K 31/519* (2013.01); *A61K 38/55* (2013.01); *A61P 9/10* (2018.01)

(58) Field of Classification Search
CPC ... A61K 31/7076; A61K 31/519; A61K 38/55
See application file for complete search history.

(56) References Cited

U.S. PATENT DOCUMENTS

| 6,423,705 B1 * | 7/2002 | Tracey | A61K 31/4709 514/221 |
| 2014/0135296 A1 | 5/2014 | Deretic et al. | |

FOREIGN PATENT DOCUMENTS

WO 2007134271 A2 11/2007

OTHER PUBLICATIONS

Yang, et al., "The Highly Selective Caspase-1 Inhibitor VX-765 Provides Additive Protection Against Myocardial Infarction in Rat Hearts When Combined With a Platelet Inhibitor," Journal of Cardiovascular Pharmacology and Therapeutics, 2017, pp. 574-578, vol. 22(6).

* cited by examiner

*Primary Examiner* — Pancham Bakshi
(74) *Attorney, Agent, or Firm* — Matthew J. Parker; Maynard Cooper & Gale, P. C.

(57) ABSTRACT

The present disclosure generally pertains to methods of treating myocardial infarct involving administering a platelet anti-aggregate, a cysteine-aspartic protease inhibitor, and reperfusion therapy. In certain embodiments, the platelet anti-aggregate is at least one $P2Y_{12}$ receptor antagonist or Glycoprotein IIb/IIIa inhibitor, the cysteine-aspartic protease inhibitor is selected from the group consisting of Caspase-1, 4, 5, 11 and 12 inhibitors, and reperfusion therapy is percutaneous coronary intervention. In certain embodiments, the at least one $P2Y_{12}$ receptor antagonist is selected from the group consisting of cangrelor, ticagrelor, clopidogrel and prasugrel. The disclosed methods provide an improved cardioprotective effect against infarction when compared with the current standard of care.

4 Claims, 10 Drawing Sheets

COMBINED ADMINISTRATION OF CYSTEINE-ASPARTIC PROTEASE INHIBITORS WITH P2Y12 RECEPTOR ANTAGONISTS PROTECTS THE HEART AGAINST MYOCARDIAL INFARCTION

CROSS-REFERENCE TO RELATED APPLICATION

This application claims priority to U.S. Provisional Patent Application No. 62/602,546, entitled "Combined Administration of the Caspase-1 Inhibitor VX-765 with $P2Y_{12}$ Receptor Antagonists Protects the Heart against Myocardial Infarction" and filed on Apr. 27, 2017, which is incorporated herein by reference.

BACKGROUND OF THE INVENTION

Acute myocardial infarction (AMI) is a major cause of morbidity and mortality worldwide. Current standard of care for patients identified with AMI is rapid percutaneous coronary intervention (PCI) to open the occluded vessel and administration of $P2Y_{12}$-receptor antagonists to prevent platelet aggregation. The overall goal of the conventional approach is to limit further myocardial cell death by maintaining patency of the deployed stent. However, despite this intervention, approximately 25% of patients presenting with left anterior descending coronary artery (LAD) occlusion, still experience poor outcomes with roughly equivalent numbers of patients either dying within one year or surviving only to suffer from chronic heart failure. The primary cause of these complications seems to be death of cardiac muscle which causes an overall loss of the heart's pumping power.

Recent intensive investigation has gone into identifying new approaches to further preserve myocardial tissue viability in these patients. Studies focused on understanding the mechanisms of myocardial tissue death during ischemia/reperfusion (I/R) injury have revealed multiple potential targets for intervention. Opening of mitochondrial transition pores, intracellular calcium overload and impartment of $Na^+/K^+$ ATPase leading to cell swelling have been all implicated in myocardial tissue death. In addition, other factors such as reactive oxygen and nitrogen species (RS) signaling, activation of a bioenergetics switch involving dysfunctional glyceraldehyde-3-phosphate dehydrogenase (GAPDH) activity, activation of programmed cell death, and inflammation-induced tissue necrosis have all been implicated at various stages of I/R injury. Considering the complex nature of I/R injury, incrementally improving patient outcomes will likely require simultaneously targeting pathways involved in preserving myocardial tissue viability. Recent evidence suggests that the inflammasome-Caspase-1 axis is an underappreciated source of cell death during I/R. Beyond the canonical role of Caspase-1 in activating inflammation via cleavage of pro-interleukins IL-1β and IL-18, this cysteine protease also has the potential to cleave glycolytic enzymes such as GAPDH and mitochondrial enzymes affecting RS signaling pathways, as well as activating rapid inflammatory cell death (pyroptosis). As such, there is renewed interest in selectively targeting Caspase-1 as a potential AMI therapeutic.

The canonical role of the Inflammasome-Caspase-1 axis is to initiate inflammation by cleaving the pro-forms of interleukins IL-1β and IL-18, and activation of pyroptosis. Initial evidence for a role for Caspase-1 in driving I/R injury came from experiments showing administration of a pan-caspase-1 inhibitor (zVAD) reduced infarct size in rat models of coronary I/R. The critical role for Caspase-1 was reinforced by the observation that a selective Caspase-1 inhibitor (YVAD) protected human atrial explants from simulated I/R. In addition, YVAD also reduced infarct size in an open chest rabbit model. Moreover, mice harboring a caspase-$1^{-/-}$ mutation displayed reduced infarct size and attenuated left ventricular remodeling in models of I/R. Conversely, Caspase-1 overexpression in mice increased infarct size by 50%. Also, Caspase-1 inhibition in renal and brain models of I/R injury has also been shown to be protective. However, the positive results associated with inhibiting Caspase-1 during I/R injury have been overshadowed by conflicting evidence generated in studies targeting components both up- and down-stream of Caspase-1. These discrepancies might be related to an experimental approach targeting only a single component of the up- or down-stream pathways. For example, targeting only NLRP3 ignores the presence and possible contributions of other NLRs in responding to danger signals elicited during I/R injury leading to inflammasome assembly along with Caspase-1 activation. Similarly, targeting only a single downstream effector of Caspase-1 such as IL-1β or IL-18 (or their putative receptors) ignores possible parallel contributions from other non-canonical Caspase-1 proteolytic targets, such as activation of Gasdermin D-executed pyroptosis. Based on the panoply of up-stream pathways that activate Caspase-1 and the multiple potential effectors lying downstream, Caspase-1 is uniquely suited as the optimal target for eliminating injury from inflammasome formation.

There is a need for new therapeutic modalities aimed at further improving AMI patient outcomes.

SUMMARY OF INVENTION

A first aspect of the present invention is a method of treating infarct in a subject in need thereof comprising the steps of administering at least one platelet anti-aggregate, administering at least one cysteine-aspartic protease inhibitor; and, administering reperfusion therapy. In a first embodiment the first aspect of the present invention, the platelet anti-aggregate is at least one $P2Y_{12}$ receptor antagonist. Alternatively, the platelet anti-aggregate is at least one Glycoprotein IIb/IIIa inhibitor. In a second embodiment of the first aspect of present invention, cysteine-aspartic protease inhibitor is selected from the group consisting of Caspase-1, 4, 5, 11 and 12 inhibitors. In this second embodiment, the cysteine-aspartic protease inhibitor is at least one Caspase-1 inhibitor. In another embodiment, Caspase-1 inhibitor is selected from the group consisting of (S)-1-((S)-2-{[1-(4-amino-3-chloro-phenyl)-methanoyl]-amino}-3,3-dimethyl-butanoyl)-pyrrolidine-2-carboxylic acid ((2R,3S)-2-ethoxy-5-oxo-tetrahydro-furan-3-yl)-amide (VX-765), emricasan, and (S)-3-({1-[(S)-1-((S)-2-([1-(4-amino-3-chlorophenyl)-methanoyl]-amino)-3,3-dimethyl-butanoyl)-pyrrolidin-2yl]-methanoyl}-amino)-4-oxo-butyric acid (VRT-043198). In a third embodiment of the first aspect of the present invention, reperfusion therapy is percutaneous coronary intervention. In certain embodiments, the reperfusion therapy is administered after administration of the at least one $P2Y_{12}$ receptor antagonist and the at least one cysteine-aspartic protease inhibitor. In certain embodiments, the at least one $P2Y_{12}$ receptor antagonist is selected from the group consisting of cangrelor, ticagrelor, clopidogrel and prasugrel.

A second aspect of the present invention is a method of treating infarct in a subject in need thereof comprising administering a P2Y$_{12}$-receptor antagonist and a cysteine-aspartic protease inhibitor selected from the group consisting of (S)-1-((S)-2-{[1-(4-amino-3-chloro-phenyl)-methanoyl]-amino}-3,3-dimethyl-butanoyl)-pyrrolidine-2-carboxylic acid ((2R,3S)-2-ethoxy-5-oxo-tetrahydro-furan-3-yl)-amide (VX-765) and emricasan, followed by reperfusion therapy. In certain embodiments, the P2Y$_{12}$ receptor antagonist is selected from the group consisting of cangrelor, ticagrelor, clopidogrel and prasugrel.

A third aspect of the present invention is a method of treating infarct in a subject in need thereof comprising administering a P2Y$_{12}$-receptor antagonist and a cysteine-aspartic protease inhibitor selected from the group consisting of (S)-3-({1-[(S)-1-((S)-2-{[1-(4-amino-3-chlorophenyl)-methanoyl]-amino}-3,3-dimethyl-butanoyl)-pyrrolidin-2yl]-methanoyl}-amino)-4-oxo-butyric acid (VRT-043198) and emricasan, followed by reperfusion therapy. In certain embodiments, the at least one P2Y$_{12}$ receptor antagonist is selected from the group consisting of cangrelor, ticagrelor, clopidogrel and prasugrel.

BRIEF DESCRIPTION OF THE DRAWINGS

The disclosure can be better understood with reference to the following figures.

DESCRIPTION OF THE PREFERRED EMBODIMENT

Figure 1:
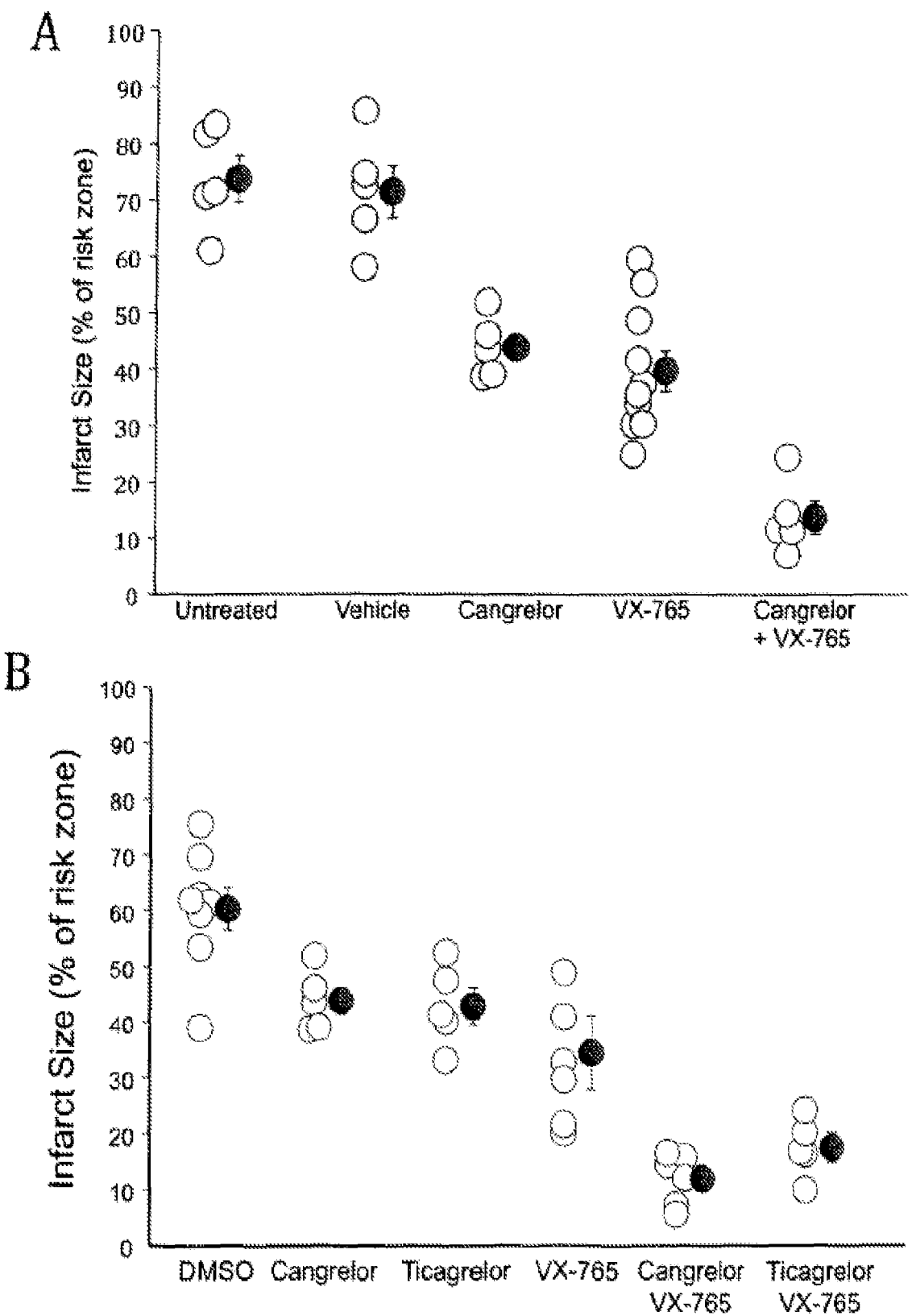
FIG. 1 is a graphical illustration depicting that combining cangrelor and VX-765 or ticagrelor and VX-765 confers additive cardioprotection. A. Infarct size (tetrazolium staining method) in anesthetized open-chest rats treated with VX-765 prior to 60 min of ischemia followed by 2 h reperfusion. B. Shows infarct size in anesthetized rats treated with VX-765 5 min prior to reperfusing the heart after 60 min of ischemia.

The present disclosure generally pertains to methods of treating myocardial infarct involving administering a platelet anti-aggregate, a cysteine-aspartic protease inhibitor, and reperfusion therapy.

Applicants have discovered that combinatorial inhibition of a cysteine-aspartic protease inhibitor (e.g., Caspase-1), along with a platelet anti-aggregate (e.g., P2Y$_{12}$ receptor antagonists), represent a novel therapeutic target during I/R injury. Hence, Applicants' submit that one aspect of the present invention is the co-administration at least 5 min prior to therapeutic reperfusion of an inhibitor of active Caspase-1 VX-765, which is available as a clinical grade pro-drug that has passed Phase I and II clinical trials, and the P2Y$_{12}$-receptor antagonist cangrelor or ticagrelor confer more cardioprotection than the P2Y$_{12}$-receptor antagonist alone (current standard of care). As shown below, for example, this combination therapy after 60-min ligation of the LAD followed by either 120-min (acute model) or 3-days (chronic model) of reperfusion in senile (i.e., retired breeders) male rats to simulate the age demographic of the AMI population. Importantly, the combination therapy was delivered 5 min prior to reperfusion to simulate the clinical standard care. Applicants examined whether administration of the VX-765 targeted canonical and emerging Caspase-1 effector proteins (e.g., IL-10, glycolytic enzymes and mitochondrial enzymes) and documented functional consequences such as LDH release and protein oxidation.

As used herein, the term "treatment" or "treating" is defined as an alleviation of symptoms associated with a disorder or disease, or inhibition of further progression or worsening of those symptoms, or prevention or prophylaxis of the disease or disorder, or curing the disease or disorder.

As used herein, the term "combination" is defined as having sufficient titers of both a P2Y$_{12}$ receptor inhibitor and a Caspase-1 inhibitor in the blood when the occluded coronary artery is reperfused.

As used herein, the term "administering" means delivery of a composition orally, intravenously, by injection, by inhalation, or by other means known in the art. Suitable means of delivery may depend on the composition. For example, in certain embodiments, Caspase-1 inhibitors are administered by intravenous injection of the Caspase-1 inhibitor. In some embodiments, Caspase-1 is administered at least 5 minutes prior to reperfusion. As another example, in another embodiment, a P2Y$_{12}$ inhibitor is administered intravenously (e.g., for cangrelor) or orally (e.g., for ticagrelor, clopidogrel, etc.). In certain embodiment, administration of a P2Y$_{12}$ inhibitor is early enough to effect loss of platelet reactivity at the time of reperfusion.

As used herein, the term "co-administering" is defined as having both agents present at a therapeutic concentration at the time of reperfusion.

As used herein, the term "infarct" is defined as death of some of the heart muscle which weakens the heart and can leading to death of the patient or disabling heart failure. Dead heart muscle does not contract nor does it regenerate. The less heart muscle that dies, the better the patient's prognosis.

As used herein, the term "subject" is defined as an individual whose reactions or responses with respect to introduction of an agent are studied.

The present disclosure pertains to methods of treating myocardial infarction.

The present disclosure discloses a method of treating infarct in a subject in need thereof comprising the steps of administering at least one platelet anti-aggregate, administering at least one cysteine-aspartic protease inhibitor; and, administering reperfusion therapy.

The amount of time elapsed between administering the platelet anti-aggregate and the cysteine-aspartic protease inhibitor can range from 0 to 120 minutes depending on the $P2Y_{12}$ inhibitor employed.

The amount of time elapsed between administering the cysteine-aspartic protease inhibitor and the reperfusion therapy can range from 5 to 60 minutes.

Suitable methods of administering the $P2Y_{12}$ platelet anti-aggregate include, but are not limited to oral or intravenous as recommended by the manufacturer for use in percutaneous intervention for acute coronary thrombosis (PCI).

Amounts of $P2Y_{12}$ platelet anti-aggregate suitable for use in the first method of the present invention are those recommended by the manufacturer use in PCI.

Suitable methods of administering the cysteine-aspartic protease inhibitor include, but are not limited to intravenous or oral administration such that a Caspase-1 inhibitory plasma titer has been achieved at the moment of reperfusion.

Amounts of cysteine-aspartic protease inhibitor VX-765 suitable for use in the first method of the present invention the range of 32 mg/kg body weight or greater.

Suitable methods of administering the reperfusion therapy include, but are not limited to PCI.

The platelet anti-aggregate and the can be at least one $P2Y_{12}$ receptor antagonist approved for use in PCI.

The cysteine-aspartic protease inhibitor can be pyroptosis-associated caspases selected from the group consisting of Caspase-1, 4, 5, 11 and 12 inhibitors, preferably Caspase-1. The Caspase-1 inhibitor can be selected from the group consisting of (S)-1-((S)-2-{[1-(4-amino-3-chloro-phenyl)-methanoyl]-amino}-3,3-dimethyl-butanoyl)-pyrrolidine-2-carboxylic acid ((2R,3S)-2-ethoxy-5-oxo-tetrahydro-furan-3-yl)-amide (VX-765), i.e., oral pro-drug form of the drug and (S)-3-({1-[(S)-1-((S)-2-{[1-(4-amino-3-chlorophenyl)-methanoyl]-amino}-3,3-dimethyl-butanoyl)-pyrrolidin-2yl]-methanoyl}-amino)-4-oxo-butyric acid (VRT-043198), i.e., non-oral/active form of the drug.

Reperfusion therapy as used herein refers to a medical treatment capable of restoring blood flow, either through or around, blocked arteries, typically after a heart attack (myocardial infarction) (MI). Reperfusion therapy includes drugs and surgery. The preferable means of accomplishing reperfusion therapy is percutaneous coronary intervention.

The present disclosure also discloses a method of treating infarct in a subject in need thereof comprising the steps of administering at least one cysteine-aspartic protease inhibitor, administering at least one platelet anti-aggregate, and administering reperfusion therapy. In certain embodiments, the at least one cysteine-aspartic protease inhibitor is selected from the group consisting of Caspase-1, 4, 5, 11 and 12 inhibitors. In certain embodiments, the at least one platelet anti-aggregate comprises a $P2Y_{12}$ receptor antagonist. In certain embodiments, the $P2Y_{12}$ receptor antagonist is selected from the group consisting of cangrelor, ticagrelor, clopidogrel and prasugrel. In certain embodiments, the at least one platelet anti-aggregate comprises a Glycoprotein IIb/IIIa inhibitor. In certain embodiments, the reperfusion therapy comprises percutaneous coronary intervention. In certain embodiments, the at least one platelet anti-aggregate and at least one cysteine-aspartic protease inhibitor are co-administered.

The present disclosure also discloses a method of treating infarct in a subject in need thereof comprising administering a $P2Y_{12}$-receptor antagonist and the inhibitor (S)-1-((S)-2-{[1-(4-amino-3-chloro-phenyl)-methanoyl]-amino}-3,3-dimethyl-butanoyl)-pyrrolidine-2-carboxylic acid ((2R,3S)-2-ethoxy-5-oxo-tetrahydro-furan-3-yl)-amide (VX-765), followed by reperfusion therapy.

The present disclosure also discloses a method of treating infarct in a subject in need thereof comprising administering a $P2Y_2$-receptor antagonist and the inhibitor(S)-3-({1-[(S)-1-((S)-2-{[1-(4-amino-3-chlorophenyl)-methanoyl]-amino}-3,3-dimethyl-butanoyl)-pyrrolidin-2yl]-methanoyl}-amino)-4-oxo-butyric acid (VRT-043198), followed by reperfusion therapy.

EXAMPLES

In Situ Open-Chest LAD Occlusion, 60-Min Ischemia/120-Min Reperfusion

Using previously established methods, senile male Sprague-Dawley rats (retired breeders) weighing approximately 500 grams were anesthetized with 100 mg/kg intraperitoneal sodium pentobarbital, and anesthetic plane confirmed by breathing pattern and absence of toe-pinch reflex. Additional intravenous boluses of 5 mg/kg were administered approximately every 30-min to maintain a surgical plane of anesthesia. Rectal temperature was measured continuously and animals maintained between 37-38° C. with a heating pad. Animals were intubated through tracheotomy and positive pressure ventilation initiated with 100% oxygen. Catheters were inserted into a carotid artery for measurement of blood pressure and into a jugular vein for administration of supplemental anesthesia and drugs, or blood sampling. Chests were opened in the fourth left intercostal space. The heart was exposed by opening the pericardium and a snare was placed around the LAD. The snare was tightened to occlude the artery for 60-min and then it was loosened to reperfuse the artery for 120-min. Animals were humanely euthanized by exsanguination during deep anesthesia at protocol terminus.

The heart was removed from the chest and mounted on a Langendorff apparatus where it was perfused with normal saline. The coronary branch was re-occluded and 15 μm fluorescent microspheres were infused into the aortic perfusate to identify the ischemic risk zone as the non-fluorescent region. The heart was then fast-frozen and sectioned into 1 mm thick slices which were incubated in triphenyltetrazolium chloride (TTC) which stains living (viable) tissue deep red. The volume of unstained, infarcted tissue in each slice was measured as was the volume of ischemic tissue or risk zone identified as non-fluorescent tissue. The total volume of infarct was expressed as a percent of the total ischemic volume for each heart.

Applicants have previously reported that administration of VX-765 at 16 mg/kg body weight 30-min prior to the onset of ischemia is extremely cardioprotective. Considering that VX-765 is a pro-drug that must be converted enzymatically to its active form and the kinetics of conversion are unknown, Applicants determined higher doses (compared to Applicants' previous study) might be necessary in order to elicit cardioprotection when administered immediately prior to reperfusion. Thus, Applicants tested a higher dose of VX-765 (32 mg/kg). VX-765 or its vehicle control (DMSO) were administered as an intravenous bolus 5-min prior to reperfusion. The P2Y$_{12}$ receptor antagonists were administered as either an intravenous (cangrelor) or intraperitoneal (ticagrelor) single bolus 10-min prior to reperfusion. For cangrelor, the initial bolus was followed by continuous intravenous infusion for the duration of the protocol. Six groups of animals were tested (n>5 per group) using the following experimental conditions: 1) Vehicle control DMSO (the VX-765 solvent) was administered as (1.0 mL of 100% DMSO)×(kg body weight) with the final infusion volume adjusted to 0.9 mL with normal saline; 2) cangrelor, 60 μg/kg intravenous bolus and 6 μg/kg/min continuous infusion; 3) ticagrelor, 30 mg/kg intraperitoneal bolus; 4) VX-765, 32 mg/kg; 5) ischemic postconditioning with 3 cycles of 30 second reperfusion plus 30 second coronary occlusion; 6) combination of ticagrelor plus ischemic postconditioning; 7) combination of cangrelor and VX-765; 8) combination of ticagrelor and VX-765. Other timings are contemplated, but not discussed, herein, for example infusing with VX-765 at 30-min post reperfusion followed by an additional 90-min of reperfusion.

In Situ Open-Chest LAD Occlusion, 60-Min Ischemia Followed by Chest Closure and 3-Days Reperfusion In this model, rats were anesthetized with sodium pentobarbital and prepared as above. Ultrasonography was performed on spontaneously breathing animals using a Vevo 770 System equipped with a 60 MHz probe (FUJIFILM VisualSonics Inc., Toronto, ON, Canada). The probe was placed on the anterior chest wall and six images at the level of the posterior papillary muscle (3 in short-axis-view and 3 in long-axis-view) were recorded. Long- and short-axis cross-sectional images of the left ventricle were displayed and an M-mode cursor was placed across the images to record motion of the anterior and posterior walls for measurement of end-systolic and end-diastolic chamber dimensions. Fractional shortening was calculated as the difference between end-systolic and end-diastolic dimensions normalized for end-diastolic dimension and averaged over six consecutive cardiac cycles.

Upon completion of ultrasonography, animals were intubated for ventilation with 100% oxygen, and surgery was performed under semi-sterile conditions. A jugular vein was exposed and cannulated and the LAD isolated as noted above. Two groups were evaluated: 1) DMSO (same concentration as described above) as a bolus 5-min prior to reperfusion and 2) cangrelor (same concentration as above) infused as an intravenous bolus 10-min prior to reperfusion followed by a 2-hours infusion combined with VX-765 (same concentration as above) infused as a bolus 5-min prior to reperfusion. Ligatures were released to initiate reperfusion and following closure of thoracotomy animals were allowed to recover for 3-days after which animals were re-anesthetized with sodium pentobarbital. Ultrasonography was performed as described above. Animals were then humanely euthanized for infarct size measurement as described above.

Ex Vivo, Isolated Heart 40-Min Global Ischemia/120-Min Reperfusion

To examine effects of VX-765 on blood-free isolated hearts, rats were anesthetized as described above. Animals were intubated through tracheotomy and positive pressure ventilation initiated with 100% oxygen. A thoracotomy was performed and the heart was quickly excised from the chest cavity for mounting on a Langendorff apparatus (within one minute). The coronary arteries were retroperfused with Krebs buffer through the aortic root and a latex balloon was placed in the lumen of the left ventricle allowing volume adjustment to 100 mmHg peak ventricular pressure. After a 20-min period of equilibration, perfusion was stopped for 40-min to induce global ischemia. The heart was maintained in a water-jacketed chamber filled with buffer during the occlusion period at a constant temperature of 37° C. Perfusion was re-initiated and continued for 120-min. The balloon was deflated at the beginning of reperfusion so subendocardial perfusion would not be impaired by any elevation in luminal diastolic pressure. The balloon was reinflated to zero diastolic pressure (unstressed ventricular volume) so final developed pressure could be measured. The coronary effluent was sampled immediately prior to ischemia, immediately at reperfusion, and serially thereafter every 20-min. The heart was perfused with buffer containing either vehicle (DMSO) or VX-765 for 10-min prior to ischemia and again during reperfusion. Two groups were tested: 1) DMSO vehicle control perfused at 0.5 mL/L of buffer and 2) VX-765, 30 μM final concentration. After 120 minutes reperfusion, developed pressure was measured as the difference between end-systolic and end-diastolic left ventricular pressure with a transducer attached to the intraventricular balloon. Infarct size was measured as above. Collected effluent was analyzed for lactate dehydrogenase (LDH) as previously described. An independent aliquot was concentrated 20-fold using a 3,000 MW cut-off ultrafilter (Millipore) and assayed for IL-1β by ELISA (ThermoFisher Scientific).

In Situ Open-Chest LAD Occlusion, 60-Min Ischemia/30-Min Reperfusion

Applicants' standard in situ open chest LAD occlusion protocol was modified to examine effects of a 30-min reperfusion period on heart tissue enzymes and metabolic function. Two groups were tested with infusions occurring 5-min prior to reperfusion: 1) vehicle control DMSO (the VX-765 solvent) was administered as (1.0 mL of 100% DMSO)×(kg body weight) with the final infusion volume adjusted to 0.9 mL with normal saline; and 2) VX-765, 32 mg/kg. Immediately prior to experiment terminus, blood was collected and serum assayed by ELISA for levels of circulating IL-1β. At experiment terminus, the heart was removed from the chest and mounted on a Langendorff apparatus where it was perfused with normal saline. The coronary branch was re-occluded and 15 μm fluorescent microspheres were infused to identify the ischemic zone followed by acquisition of biopsies from both ischemic and non-ischemic zones. Viable samples were immediately prepared for high resolution respirometry using the Oroboros oxygraph O2K as previously described. In parallel, a portion of the biopsied tissue was immediately ejected into liquid nitrogen and stored at −80° C. Subsequently, tissues were homogenized and solubilized for analyses of total protein. Normalized amounts of protein were resolved by SDS-PAGE (4-20% Tris-Glycine gradient gels) and analyzed by immunoblotting using antibodies against Caspase-1, glyceraldehyde-3-phosphate dehydrogenase (GAPDH), Aldolase-A, and Hexokinase II. In a separate set of blots, samples were assayed for protein oxidation (carbonylation) using the oxidized protein western blot kit (Abcam, oxyblotting). For all blotting experiments, protein transfer membranes were first stained with Coomassie Brilliant Blue (CBB) and analyzed on the LiCor Odyssey for total protein levels. These CBB data were used to normalize all immuno- and oxyblotting data.

Statistics

GraphPad Prism v6.1 was used for all analyses. Data are reported as mean standard error. Data were assessed for normality prior to analysis. Pairwise comparison of parametric data was performed using 2-tailed unpaired-t-test to compare two groups as indicated. One- or Two-way ANOVA was used to compare observations in two or more groups. Newman-Keuls post-hoc test was applied as necessary. Differences with a P value <0.05 were considered significant.

Treatment with a Highly Selective Caspase-1 Inhibitor Prior to the Onset of Ischemia and a $P2Y_{12}$ Receptor Antagonist Just Prior to Reperfusion Greatly Reduces Infarct Size.

In this protocol the VX-765 was test by administering it prior to the onset of ischemia. That way it could treat both ischemic and reperfusion types of injury. The results can be seen in FIG. 1A. XV-765 was administered as an intravenous bolus of 16 mg/kg 30 minutes prior to a 60 minute occlusion of a coronary branch in open chest anesthetized rats. Pilot studies revealed that infarct size reduction became independent of the dose above 16 mg/kg (data not shown). Note that the VX-765's DMSO vehicle had no effect on infarct size. Cangrelor started 10 min prior to reperfusion or VX-765 30 min prior to ischemia caused a similar reduction in infarct size. When the two treatments were combined we saw an additive effect on the infarct size. Unfortunately pretreatment is not possible in patients presenting with acute myocardial infarction (common heart attack). The blood clot occluding their coronary artery is the first indication that something is wrong and they present to hospital with ischemia in progress. Therefore we did experiments to see if a similar protection could be obtained by giving the VX-765 5 min prior to reperfusion the artery.

Combining a Highly Selective Caspase-1 Inhibitor and a $P2Y_{12}$ Receptor Antagonist During Just Before Reperfusion the Ischemic Heart Greatly Reduces Infarct Size There are three interrelated therapeutic aspects that determine successful outcomes in patients suffering from AMI. The first is opening of the vessel to restore blood flow and the second is maintaining vessel patency. Thus, the current standard of care for patients presenting with AMI involves PCI and administration of $P2Y_{12}$-receptor antagonist which not only keeps clots from forming in the stent but also exerts a powerful anti-infarct effect independent of its anticoagulant mechanism which can be seen in our figures. The third therapeutic consideration relates to minimizing cardiomyocyte death because loss of contractile mass directly leads to heart failure, a major cause of patient morbidity and mortality. Thus, novel interventions that reduce cardiomyocyte death beyond that from platelet inhibitors and early reperfusion should provide a remarkable clinical improvement both in patient survival and in amelioration of heart failure. However, the current conundrum facing the field is the question of whether PCI and administration of $P2Y_{12}$-receptor antagonists have reached a saturating level of cardioprotective therapeutic value (i.e., the system is already working at its maximal protective capacity). Thus, discovery of new clinically applicable cardioprotective interventions hinges on designing experimental models that incorporate $P2Y_{12}$-receptor antagonists and coronary reperfusion as an integral component of the protocol. Herein Applicants tested the cardioprotective utility of combining the highly selective, clinical grade Caspase-1 inhibitor VX-765 with $P2Y_{12}$-receptor antagonists in a rat model of I/R. Those experiments revealed that caspase-1 inhibition has the unique ability to add its protection to that from a $P2Y_{12}$-receptor antagonist.

Applicants first tested cardioprotective effect of combining VX-765 with $P2Y_{12}$-receptor antagonists in an open chest, non-survival model of acute I/R injury in which senile male rats were subjected to 60-min of LAD ligation followed by 120-min of reperfusion. Vehicle control or inhibitors (alone and in combination) were administered immediately prior to reperfusion and infarct size measured at experiment terminus. FIG. 1B shows I/R caused 60.3±3.8% of the risk zone to infarct in vehicle control (DMSO) animals. This level of infarction was comparable to that previously reported in untreated rats (73.7±4.1%). When administered individually the $P2Y_{12}$-receptor antagonists cangrelor or ticagrelor were equally cardioprotective. Cangrelor alone reduced infarction to 43.8±2.4% of the risk zone (p<0.001) and ticagrelor alone reduced infarction to 42.8±3.3%. Administration of the highly selective Caspase-1 inhibitor VX-765 was also cardioprotective, reducing infarction to 38.6±3.9%. Notice that the protection seen with VX-765 at reperfusion is similar to that seen when VX-765 was given prior to ischemia in FIG. 1A. These data suggest that VX-765 exerts virtually all of its cardioprotective effects during reperfusion. We did have to double the dose of the VX-765 to get this level of protection. Most likely that was due to incomplete conversion of the drug to its active form in the 5 min prior to reperfusion.

Co-administration of VX-765 with either of the $P2Y_{12}$-receptor antagonists significantly augmented cardioprotective effects when compared to each inhibitor alone. The combination of VX-765 and cangrelor reduced infarction to 11.9±1.9% and the combination of VX-765 and ticagrelor reduced infarction to 13.9±3.7%. There were no significant differences in either baseline heart rate or mean blood pressure between groups (data not shown). During coronary occlusion blood pressure tended to decrease, and there was partial recovery during reperfusion. Heart rate did not vary. These data indicate that combining VX-765 and $P2Y_{12}$-receptor antagonists immediately prior to reperfusion has additive therapeutic value.

Figure 2:
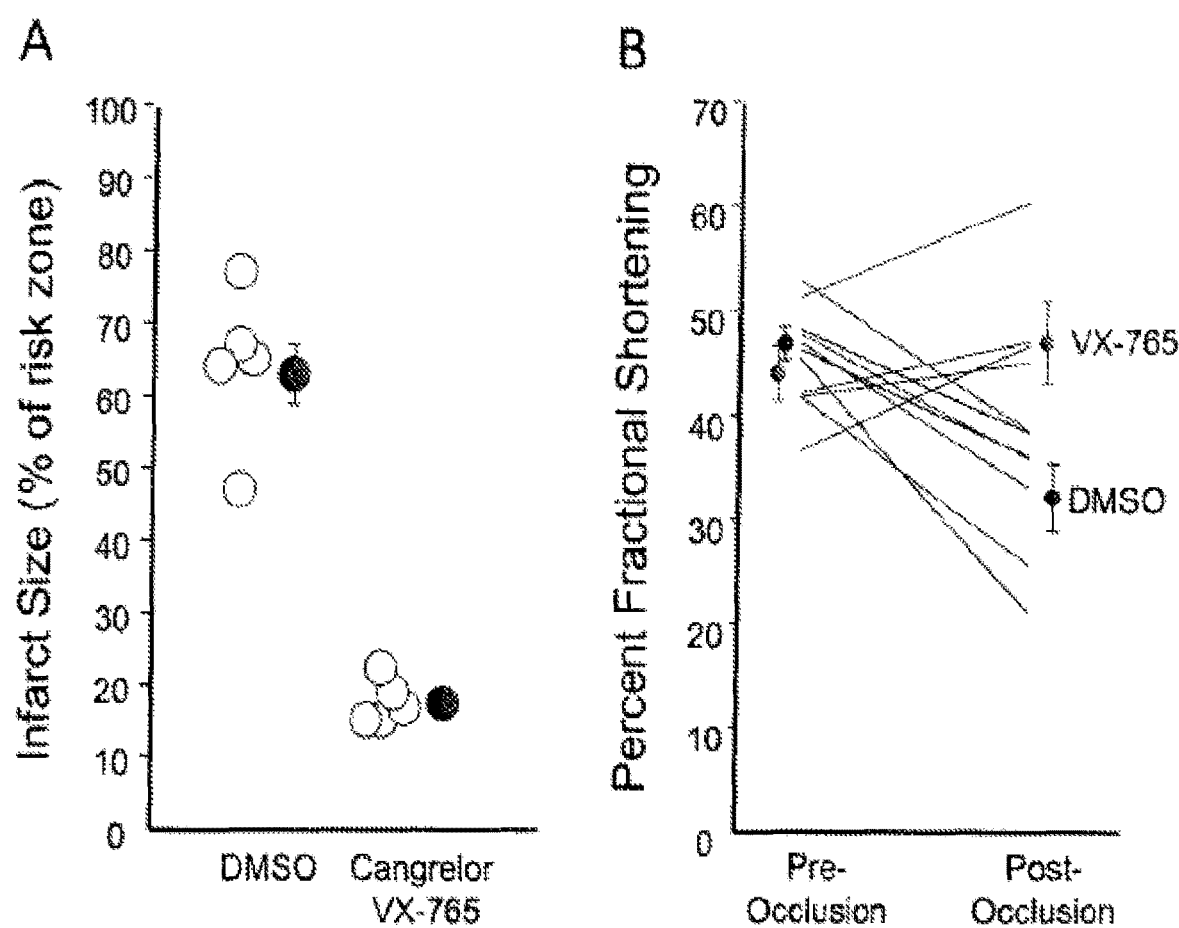
FIG. 2 is a graphical illustration portraying that combining cangrelor and VX-765 confers cardioprotection in a chronic 3-day I/R model. A. Infarct size. B) Ultrasonography assessing left ventricular function.

Combining a Highly Selective Caspase-1 Inhibitor and a $P2Y_{12}$ Receptor Antagonist During Chronic I/R Injury (3-Days Reperfusion) Provides Sustained Infarct Size Reduction Applicants next determined whether the marked cardioprotective effect of combining VX-765 and cangrelor in the acute model (120-min reperfusion) reflected a true reduction of infarction or simply a delay in its appearance. To this end Applicants tested the VX-765 and cangrelor combination in a survival model of acute I/R injury with 60-min of open-chest LAD occlusion followed by chest closure and 3-days of reperfusion. This model is advantageous because time of reperfusion is sufficient to allow for mechanical stunning to subside while minimizing the potential for infarct remodeling, which complicates assessment of injury. FIG. 2A shows that animals treated with vehicle (DMSO) has 62.9±1.9% infarction of the risk zone after 3-days, while animals treated with the combination of VX-765 and cangrelor had only 12.9±1.9% infarction. This degree of cardioprotection was similar to that seen in the acute studies (FIG. 1). These data suggest that the majority of cell death occurs during the first 120-min of reperfusion and that a single bolus of VX-765 plus cangrelor is sufficient to sustain a long-term reduction of infarct size.

As a functional readout of cardioprotection in the chronic I/R model Applicants performed chest ultrasonography to measure ventricular wall motion in the same animal prior to occlusion and after 3-days of reperfusion. FIG. 2B shows that the cardioprotection afforded by the combination of VX-765 and cangrelor resulted in protection of ventricular function. While vehicle-treated animals showed a 30% decline in fractional shortening, animals treated with the combination of VX-765 and cangrelor retained normal ventricular function. These data indicate that the combination of VX-765 and cangrelor not only decreased infarction but also that the salvaged myocardium was indeed contractile.

Caspase-1 Inhibition Targets Inflammatory Pathways in the Cardiac Tissue

Figure 3:
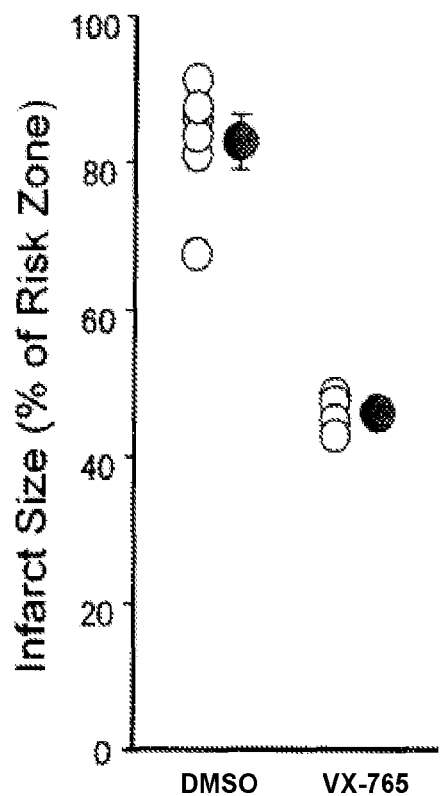
FIG. 3 is a series of graphical illustrations showing that VX-765 protects against global I/R injury in the blood free isolated buffer-perfused heart. A. Infarct size. B. Gross specimens depicting infarct areas. C. LDH release. D. Developed pressure.
Figure 3:
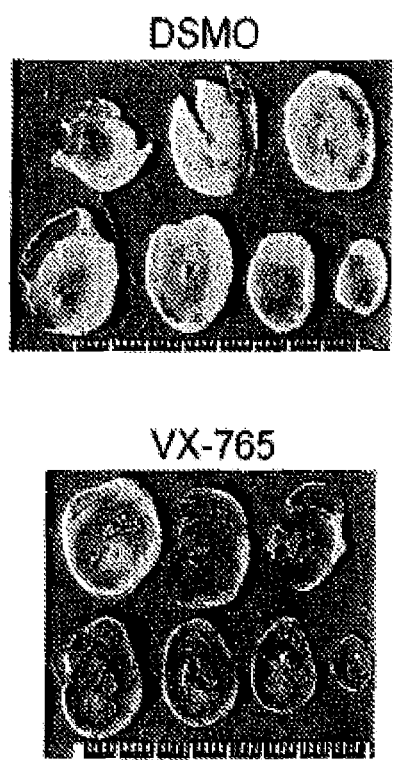
Figure 3:
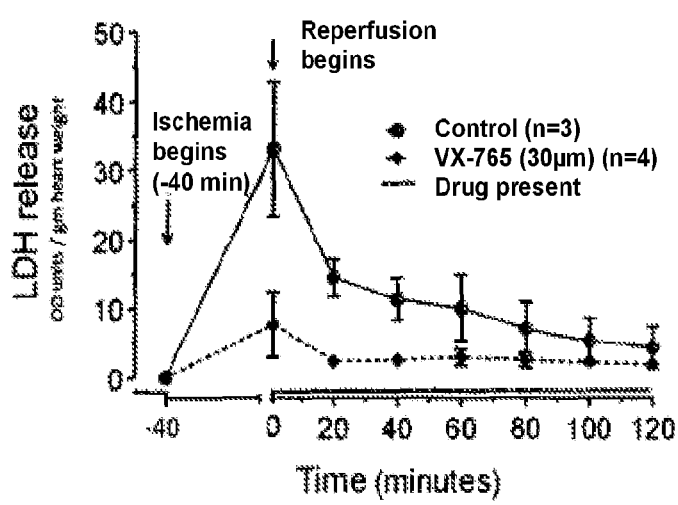
Figure 3:
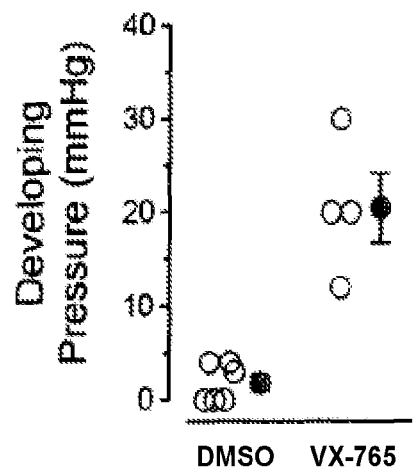

The cardioprotective effect of PCI is attributed to its role in reestablishing coronary blood flow while the effects of the $P2Y_{12}$-receptor antagonists are associated with inhibition of platelet activity. Indeed, in global ischemic isolated heart models where platelets and circulating immune cells are absent, $P2Y_{12}$-receptor antagonists exhibit no cardioprotective effects. Considering that the inflammasome-Caspase-1 axis is expressed in rat cardiac parenchymal cells, Applicants next determined whether VX-765 directly protects the heart during I/R or whether cardioprotection requires platelets and circulating immune cells. To this end Applicants used a global I/R model in isolated, blood-free rat hearts where platelets and circulating immune cells are removed. FIGS. 3A & B show infarct sizes after 40-min global ischemia followed by 120-min reperfusion where either vehicle control (DMSO) or VX-765 were added to the perfusate 5-min prior to onset of ischemia and maintained throughout reperfusion. Vehicle control hearts displayed an average infarction of 82.8±3.7% whereas VX-765 elicited a dramatic cardioprotective effect where hearts showed an average infarction of only 45.8±1.5%. The data indicate that cangrelor and VX-765 likely affect different cellular targets, which could explain why the two agents have additive cardioprotective effects.

Applicants next determined whether Caspase-1 is activated in the isolated heart global I/R model by assaying for two of its recognized downstream effectors, namely activation of inflammation (release of IL-10) and pyroptosis (release of LDH). Aliquots of the perfusion effluent exiting the heart were collected at onset of ischemia and at 20-min intervals post-reperfusion. In vehicle control hearts levels of IL-113 were not detectable by ELISA at any of the time points tested whereas LDH release peaked immediately upon reperfusion and steadily diminished thereafter (FIG. 3C, closed circles). Interestingly, in hearts treated with VX-765 the LDH release was all but abolished indicating that the hearts were protected from lytic cell death (FIG. 3C, closed diamonds). Applicants assessed functional consequences of infarction and lytic cell death by measuring left ventricular developed pressure at the end of 120-min of reperfusion. FIG. 3D shows that in agreement with the infarct size and LDH data, left ventricular function assessed as left ventricular developed pressure was better preserved in VX-765-treated hearts (1.8±0.9 mmHg in DMSO hearts and 20.5±4.2 mmHg in VX-7675-treated hearts).

Caspase-1 is Activated During I/R Injury as Evidenced by Effects on IL-1β, Glycolytic Enzyme Levels, and Mitochondrial Function The data thus far show that infarct size after 3-days of reperfusion is not different from infarct size after 2-hours of reperfusion. In addition, VX-765 administered before the onset of ischemia (pre-treatment) or at the onset of reperfusion is equally cardioprotective indicating that it protects against a reperfusion injury. To examine changes in potential Caspase-1 downstream targets Applicants modified the in situ open chest model by shortening reperfusion to 30-min after which Applicants collected blood and myocardial biopsies from previously ischemic and normal myocardium. Applicants assayed the blood for the presence of IL-113, a downstream and, therefore, surrogate, marker of Caspase-1 activation. Animals treated with vehicle (DMSO) had significantly higher levels of IL-113 in blood when compared to animals treated with VX-765 (FIG. 4A).

Figure 4:
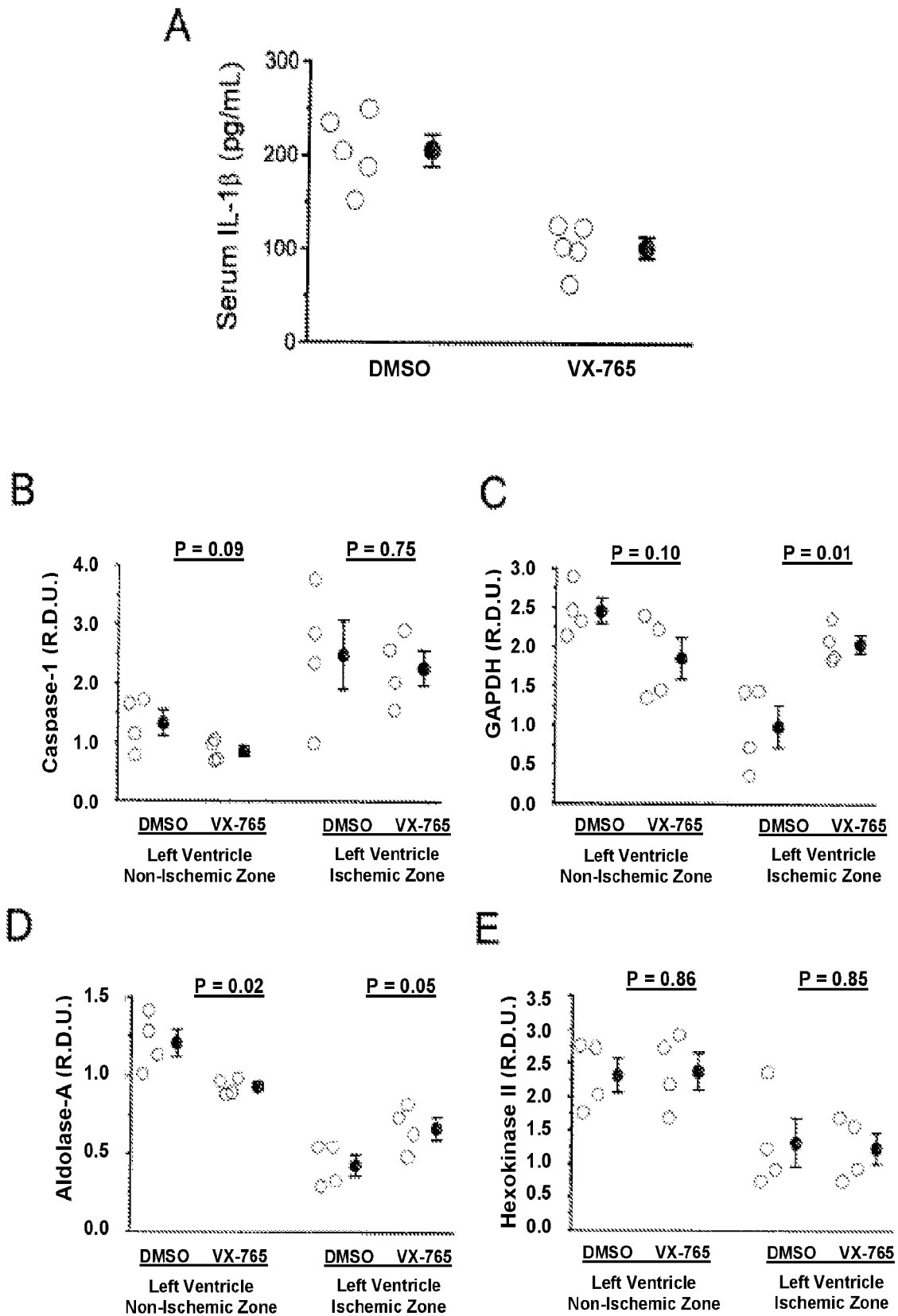
FIG. 4 is a series of graphical illustrations depicting the administration of VX-765 results in altered levels of knows Caspase-1 targeted effector proteins. A. Serum levels of IL-10. B. Tissue levels of activated caspase-1. C. Tissue levels of GAPDH. D. Tissue levels of Aldolase-A. E. Tissue levels of hexokinase II.
Figure 5:
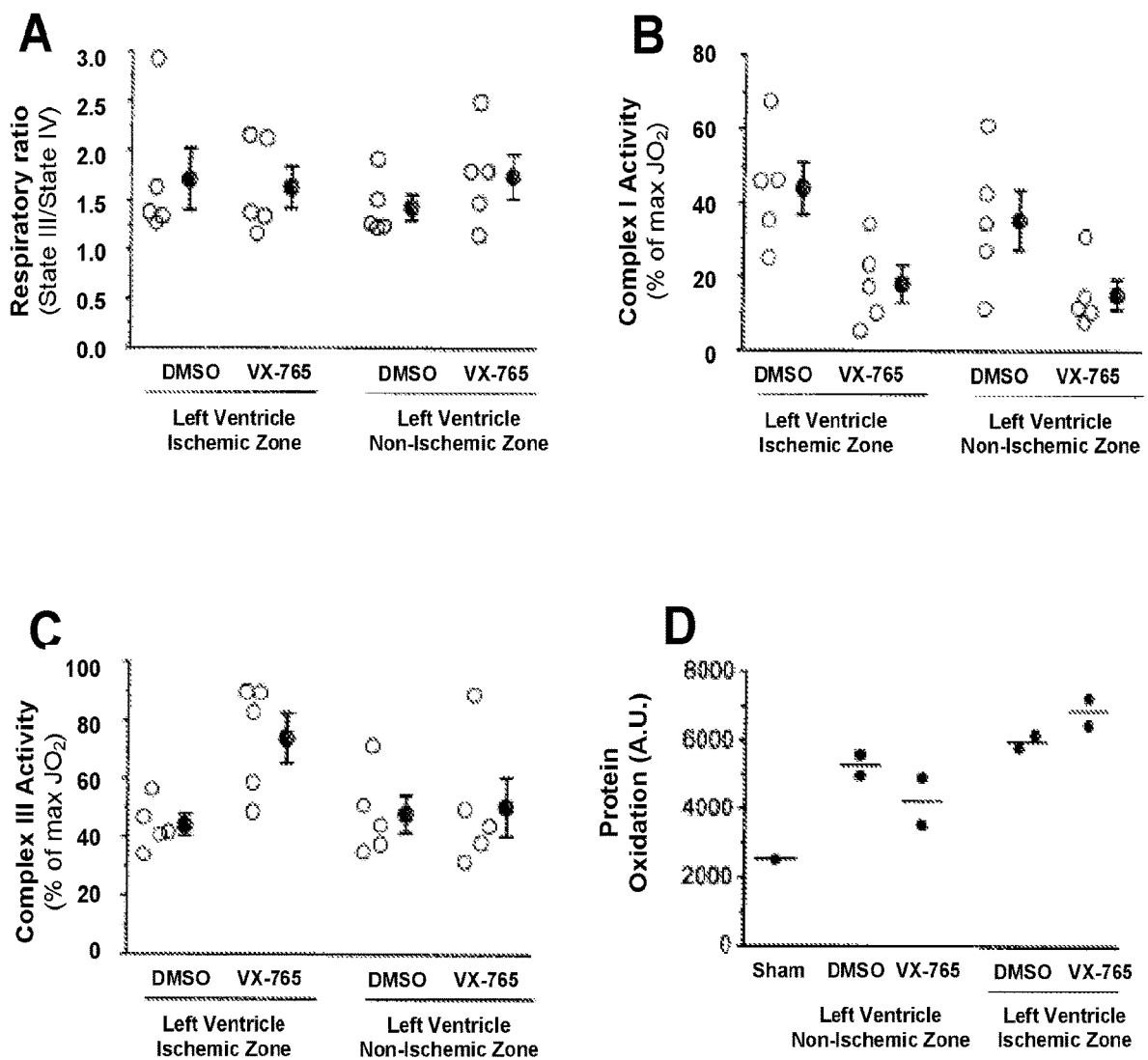
FIG. 5 is a series of graphical illustrations portraying that administration of VX-765 alters mitochondrial function in response to I/R. A. Respiratory ratio. B. Complex I activity. C. Complex III activity. D. Tissue protein oxidation levels.
Figure 6:
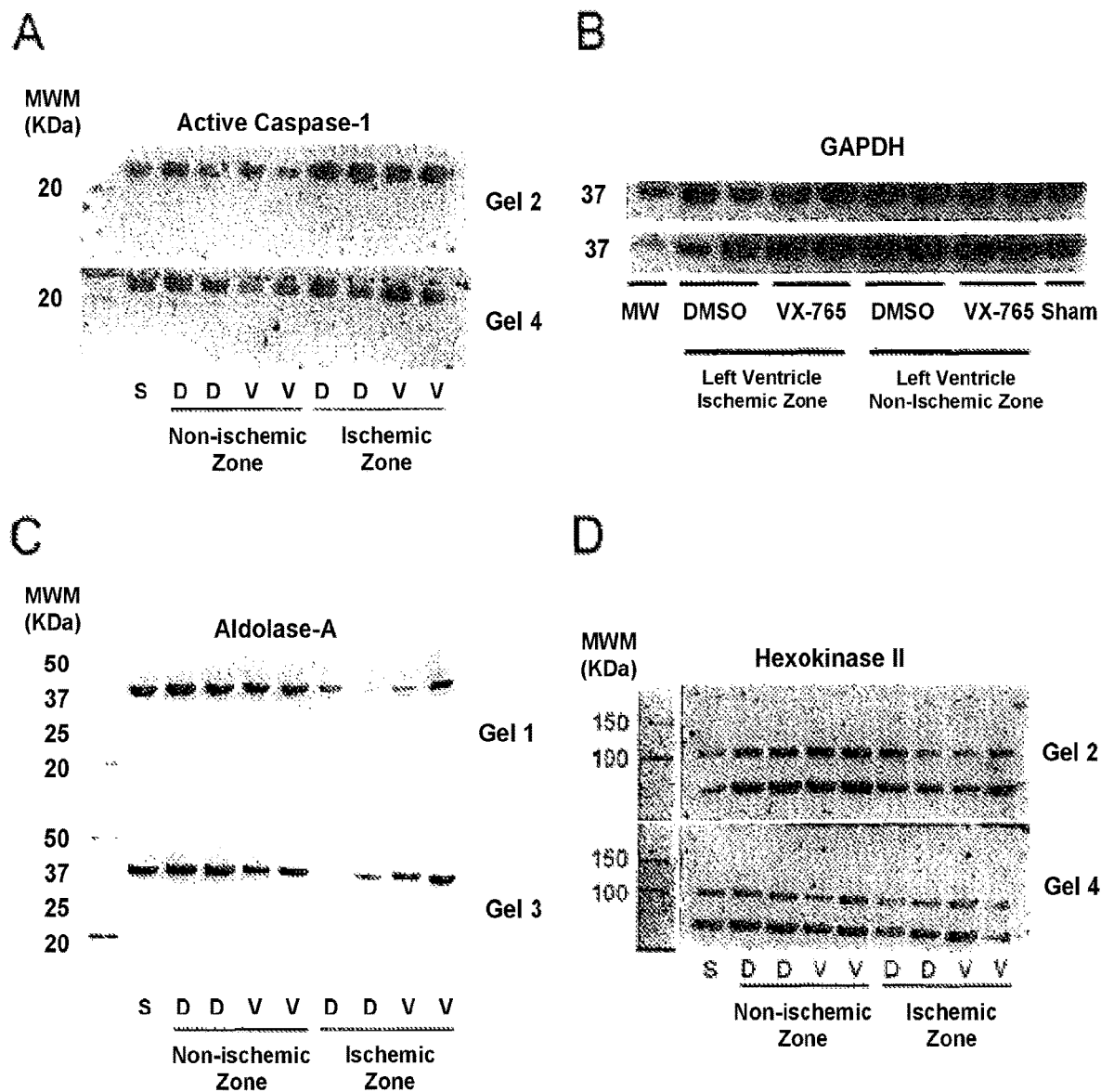
FIG. 6 shows Western blot images corresponding to FIG. 4.

Heart tissue harvested from non-ischemic and ischemic left ventricular regions was assayed for glycolytic proteins (FIG. 4) and mitochondrial function (FIG. 5). FIGS. 4B-D show results of band density quantitation after western blotting probing for active Caspase-1, two known targets of Caspase-1 that are involved in the glycolytic pathway (glyceraldehyde phosphate dehydrogenase -GAPDH- and aldolase-A), and one glycolytic protein not predicted to be targeted by Caspase-1 (hexokinase) (blots are shown in FIG. 6). Levels of active Caspase-1 were increased in ischemic tissues in both DMSO and VX-765 groups (FIG. 4B). VX-765 did not prevent Caspase-1 activation, a result supported by the fact that another Caspase-1 specific inhibitor (YVAD) inhibits enzymatic activity but not autoproteolysis of pro-Caspase-1. Treatment with VX-765 prevented degradation of GAPDH in the ischemic zone (FIG. 4C) and partially prevented degradation of aldolase-A (FIG. 4D). FIG. 4E shows that treatment with VX-765 has no effect in hexokinase II (a negative control) degradation in the ischemic zone.

Figure 7:
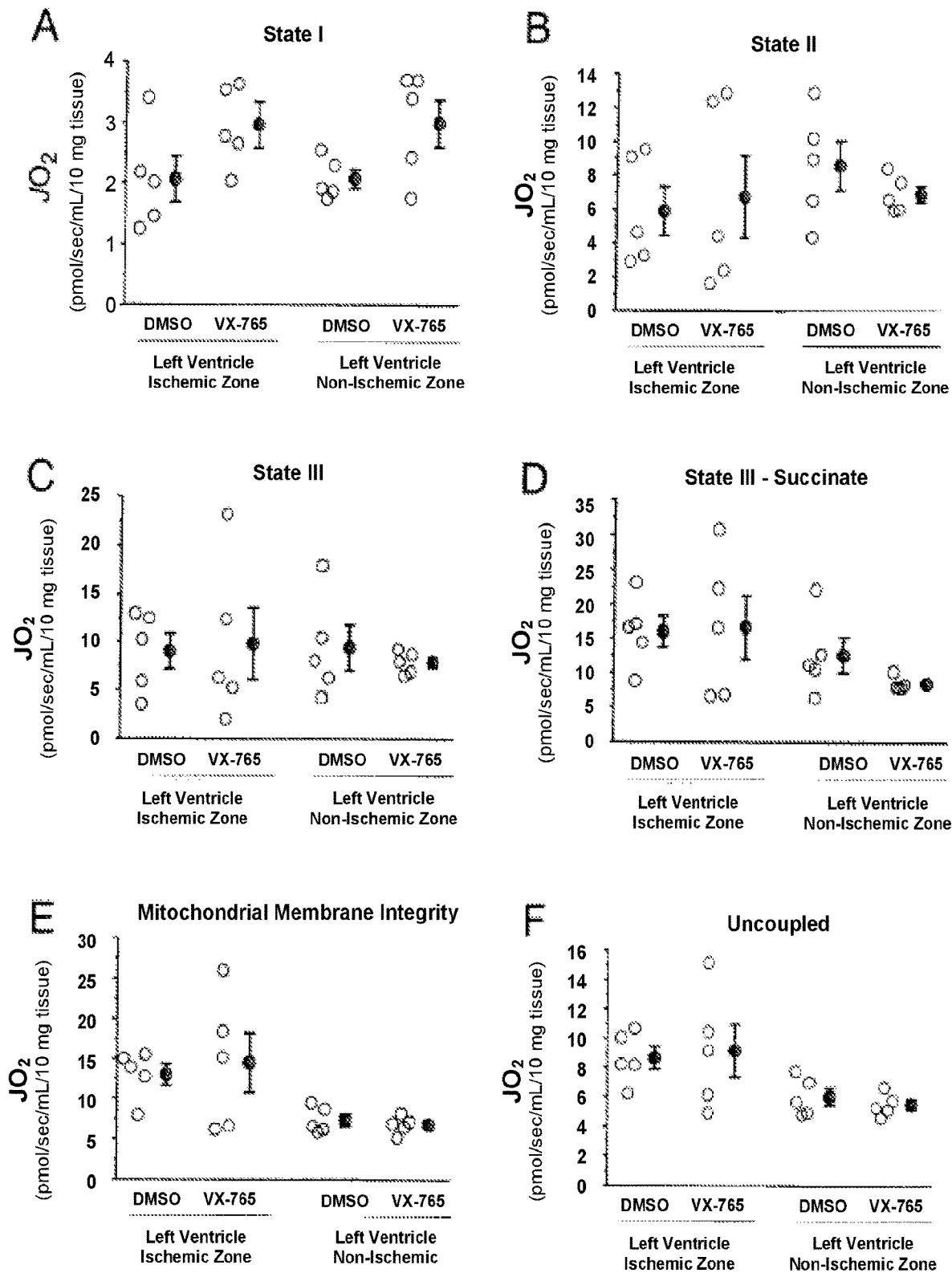
FIG. 7 is a series of graphical illustrations showing tissue mitochondrial respiration assays complementing data shown in FIG. 5.
Figure 8:
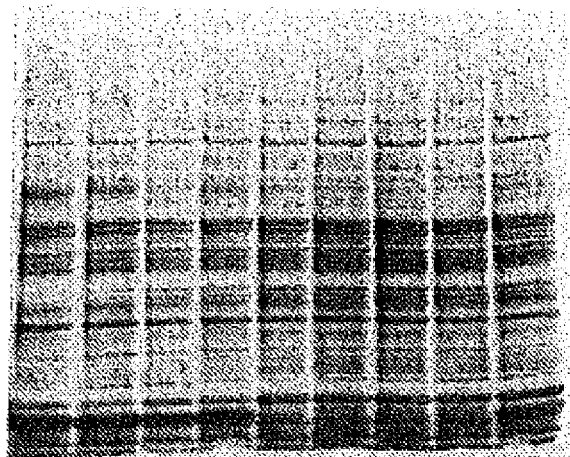
FIG. 8 depicts protein oxidation blot images use to generate data in FIG. 5D.
Figure 8:
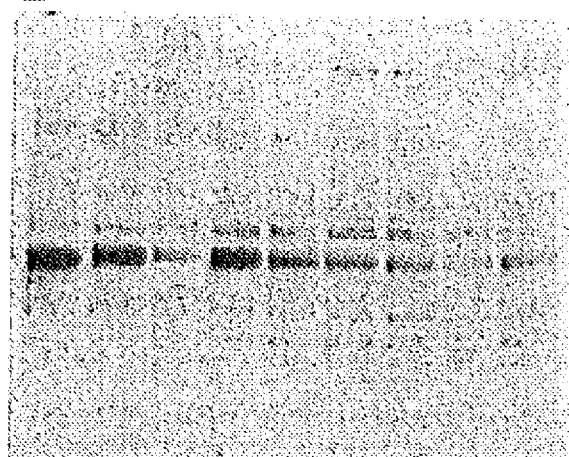
Figure 8:
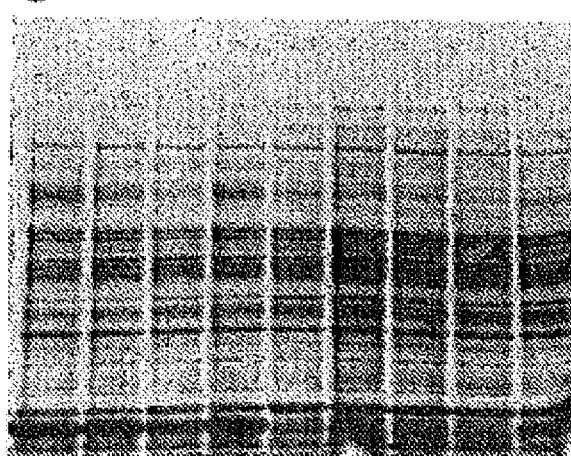
Figure 8:
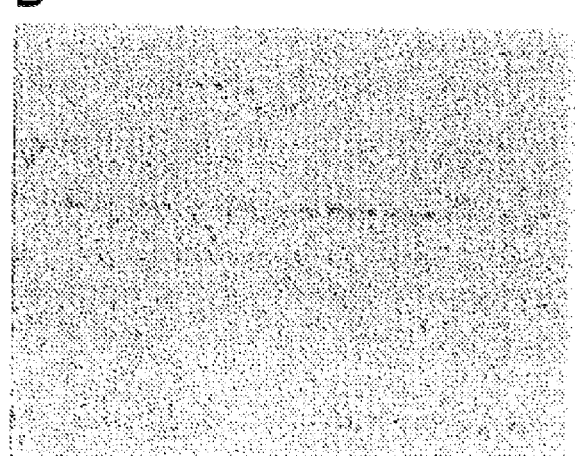

FIG. 5 shows the results of high resolution respirometry on tissue biopsies harvested as described above and as shown in FIG. 8. Tissue mitochondrial function is reported as the amount of oxygen consumed (i.e., $JO_2$). In this protocol, heart tissues are harvested 30-min after reperfusion to ensure tissue retention of mitochondrial function and permeabilized with detergents to allow direct assessment of each mitochondrial complex via addition of specific substrates (i.e., electron donors) and poisons. Using this early 30-min reperfusion time point allows differentiation of dysfunctional mitochondrial complex activities from the absolute loss of function occurring at later time points after cell death had ensued. As a further level of experimental control, mitochondrial complex activities were assayed in non-ischemic and ischemic zone tissues isolated from animals treated with vehicle control (DMSO) or the Caspase-1 inhibitor VX-765. FIG. 5A shows validation of mitochondrial fitness as determined by the respiratory ratio. The data show that tissues reperfused for 30-min were not different among all groups indicating retention of mitochondrial function which served to validate assessment of individual mitochondrial complex functions. Furthermore, none of the heart tissues from any group displayed $JO_2$ differences when the different states of mitochondrial respiration were measured in the presence of different substrates (FIG. 7). Interestingly however, assaying specific mitochondrial complex activities using energy poisons revealed the non-ischemic and ischemic tissues from animals treated with the VX-765 Caspase-1 inhibitor exhibited significantly decreased Complex-I activity compared to vehicle control (DMSO) (FIG. 5B). Moreover, a similar analysis of Complex-III activity revealed no significant differences, although the ischemic zone tissues displayed a trend towards increase in the VX-765 group compared to the vehicle control group (FIG. 5C). Together these data suggest that gross differences in mitochondrial substrate utilization are not observed in ischemic tissue, which might involve compensatory mechanisms among complexes and that inhibition of Caspase-1 decreases Complex-I activity.

The generation of reactive oxygen species (ROS) is another hallmark of mitochondrial stress during I/R. To assess generation of ROS Applicants assayed protein carbonylation from ischemic and non-ischemic tissues harvested from animals treated with vehicle control or VX-765 using the 30-min reperfusion protocol. FIG. 5D shows quantitation of band density after protein carbonylation blotting. The data show no differences in protein carbonylation.

Figure 9:
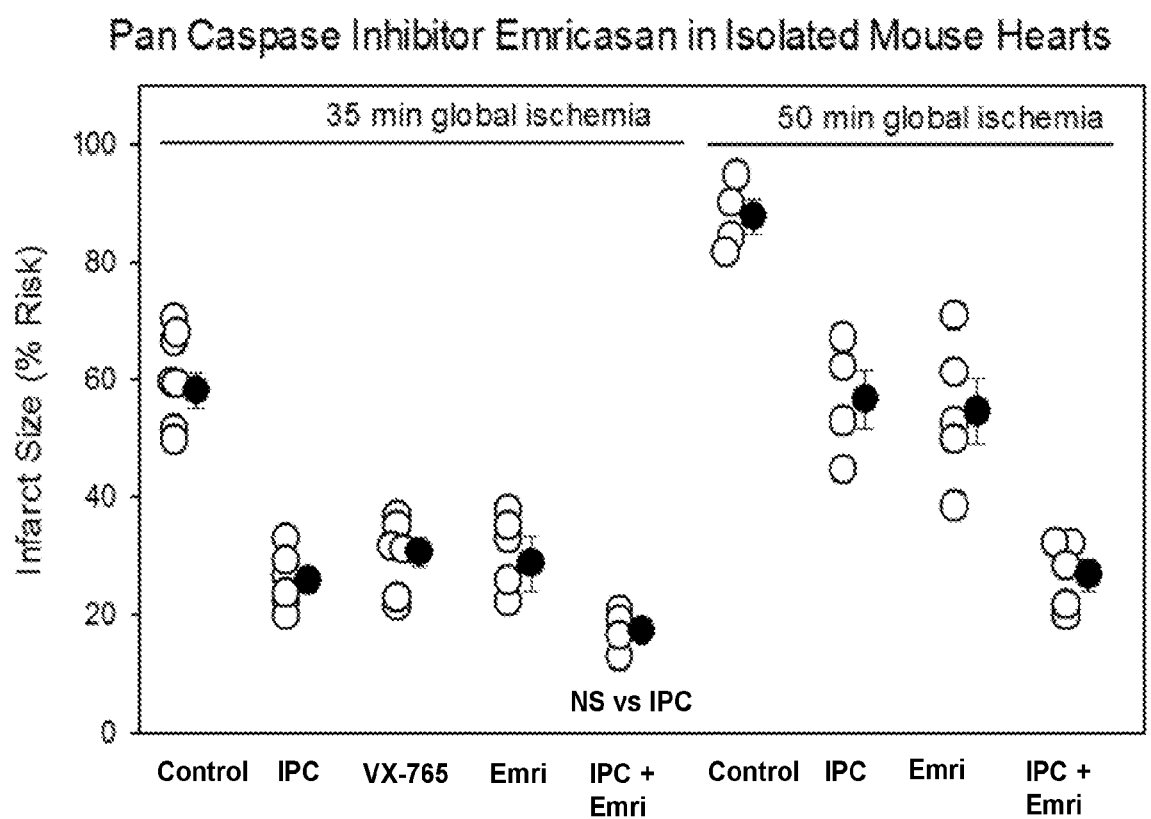
FIG. 9 is a graphical illustration depicting that emricasan an irreversible pan caspase inhibitor (includes caspase-1), VX-765 and ischemic preconditioning (IPC) similarly reduced infarct size in buffer perfused mouse hearts and that protection from emricasan plus IPC is additive.

Treatment with Emricasan and Ischemic Preconditioning Prior to the Onset of Ischemia Greatly Reduces Infarct Size Hearts were removed from pentobarbital-anesthetized C57BL/6 mice and quickly (less than 3 min) mounted on a Langendorff perfusion apparatus where they were retroperfused with Krebs buffer at 100 mmHg pressure and at 37 Deg C. After 20 min perfusion to equilibrate the perfusion was stopped to create global ischemia. After and index ischemia of either 35 or 50 min the hearts were reperfused for 2 h and infarct size was measured by triphenyltetrazolium staining. Treatments included 30 uM VX-765 for 10 min prior to ischemia and throughout reperfusion, 9 uM emricasan for the first 20 min of reperfusion only, Ischemic preconditioning (IPC) with three cycles of 5 min ischemic Plus 5 min reperfusion prior to the index ischemia, or IPC+emricasan. As shown in FIG. 9, the VX-765, IPC and emricasan were equipotent for infarct size reduction and when the index ischemia was increased to 50 min the IPC and emricasan combination showed additive protection. IPC was used as a surrogate for a platelet inhibitor because platelet inhibitors and IPC protect by the same mechanism but platelet inhibitors do not protect the blood-free isolated heart and, therefore, could not be used.

VX-765 is a prodrug of the caspase-1 inhibitor VRT-043198. It is rapidly converted by esterases in the blood and in the in situ heart preparation is very protective against infarction when administered at the onset of reperfusion. In the blood free isolated heart we had to give the VX-765 as a pretreatment. That was either because there was not enough esterase activity in the heart tissue to convert enough VX-765 to VRT-043198 to prevent a reperfusion injury or it only protected against injury during ischemia. Emricasan is an irreversible pan caspase inhibitor it blocks all known caspases including caspase-1. Emricasan at reperfusion was as protective as VX-765 pretreatment indicating 2 things. First, that the caspase-dependent injury in the isolated heart also occurs during reperfusion as is the case with the blood-perfused heart. Secondly, emricasan and VX-765 two very different molecules both protect against infarction which indicates that VX-765's protection was indeed due to caspase inhibition and not an off target effect of the molecule. Emricasan is also approved for clinical testing in patients and can serve as an alternative to VX-765, because it is not a prodrug and is an irreversible caspase inhibitor and does not need to have a prolong plasma half-life. It is possible to administer emricasan directly into the recanalized coronary artery to treat only the reperfused myocardium and reduce systemic exposure.

Figure 10:
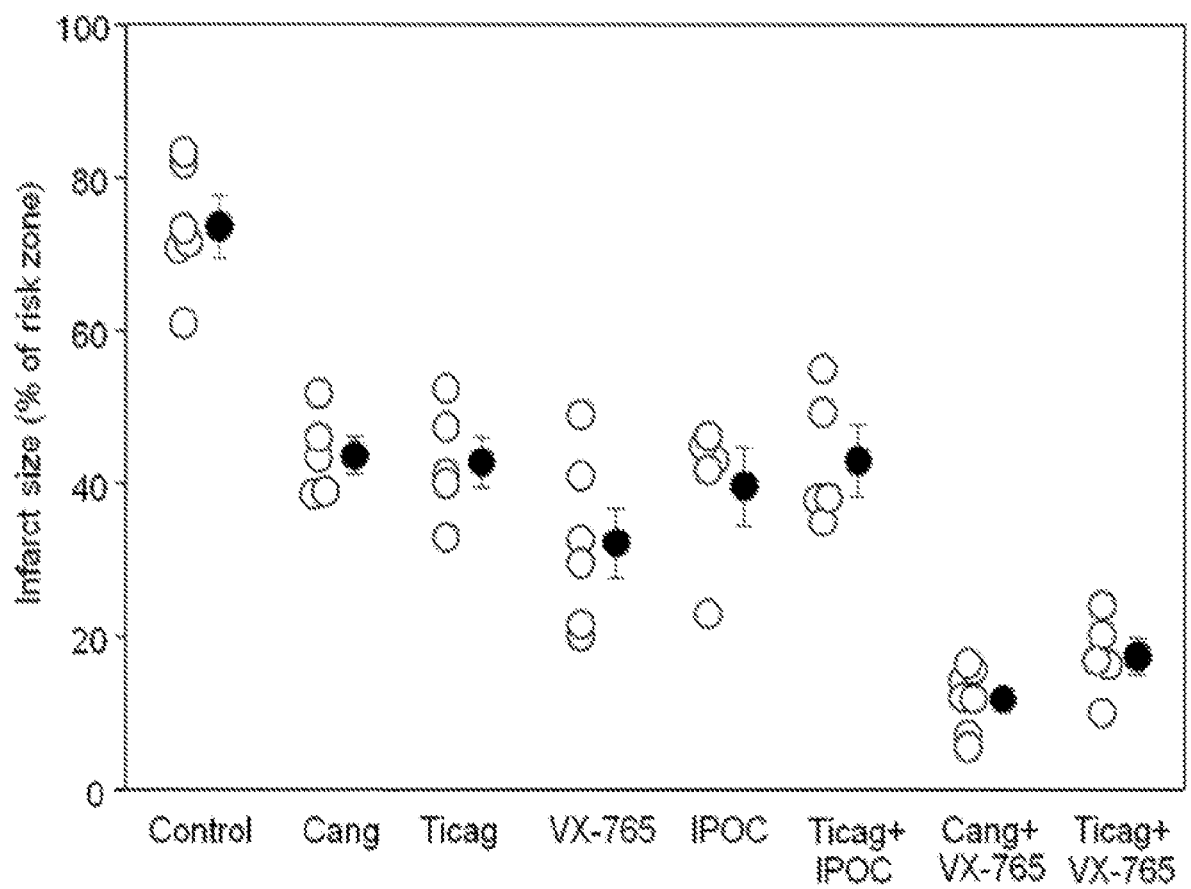
FIG. 10 is a graphical illustration depicting that ischemic postconditioning (IPOC), the platelet inhibitors ticagrelor (Ticag) and cangrelor (Cang), and VX-765 reduced infarct size in open chest rat hearts but only VX-765 could add its protection to that from the platelet inhibitors.

Treatment with Ischemic Postconditioning (IPOC) and the Platelet Inhibitor Ticagrelor (Ticag) Each Greatly Reduces Infarct Size but Cannot Add Protections The effect of ischemic postconditioning (IPOC) and the platelet inhibitor ticagrelor (Ticag) alone and in combination were tested. As shown in FIG. 10, combining IPOC with Ticag was no more protective than either alone. On the other hand VX-765 supplemented protection when combined with either Ticag or cangrelor (Cang). IPOC was three cycles of 30 seconds of reperfusion followed by 30 seconds of occlusion at the end of the 60 min index ischemia using in situ blood perfused rat hearts.

The use of a clinical grade, highly selective Caspase-1 inhibitor, VX-765, in a senile rodent acute myocardial infarction (AMI) model, as disclosed herein, has a remarkable additive cardioprotective effect against infarction when combined with a $P2Y_{12}$ inhibitor, the current standard of care. Applicants' 60 minute occlusion protocols induced near 75% infarct, which was reduced to near 15% upon co-administration of VX-765 and the $P2Y_{12}$ receptor antagonist cangrelor immediately prior to 120-min reperfusion or 3-days reperfusion. These results are striking considering that Applicants' model generates larger infarction when compared to conventional AMI protocols using 30-min occlusion to induce only ~45% infarction. Using Applicants' 60-min occlusion/120-min reperfusion model Applicants confirmed that the combination of VX-765 with another clinically relevant $P2Y_{12}$ receptor antagonist, ticagrelor, was just as cardioprotective. Note that ticagrelor by itself was no more cardioprotective than cangrelor even though cangrelor does not augment tissue adenosine by blocking its reuptake. The Applicants also saw similar protection with clopidogrel, which suggests that this is a class effect for $P2Y_{12}$ inhibitors. The Applicants' data suggests that any $P2Y_{12}$ inhibitor would similarly protect and that VX-765 would add to that protection. In addition, using the isolated perfused cardiac model of global ischemia Applicants showed that the cardioprotective effects of VX-765 appear to occur directly on the heart at least in part because did not require circulating mediators. Moreover, administration of VX-765 inhibited Caspase-1 as evidenced through expected effects on its downstream inflammatory, cell death (pyroptotic), glycolytic, and mitochondrial effectors. The methods of the present disclosure can apply to longer ischemic periods (e.g., beyond 60 minutes) and other morbidities associated with coronary artery disease (e.g., atherosclerosis, metabolic syndrome), and stent/restenosis.

Applicants demonstrate that the latest generation of platelet receptor antagonist such as ticagrelor and cangrelor display off-target effects that are cardioprotective beyond the canonical function of maintaining vessel patency. In addition, cardioprotective effects of ticagrelor, clopidogrel and cangrelor are prevented by inhibitors that target signaling cascades classically associated with post-conditioning. Applicants' disclosure demonstrates that inhibiting Caspase-1 in Applicants' model has an additive cardioprotective effect when combined with the $P2Y_{12}$ receptor antagonists cangrelor and ticagrelor.

Applicants' data using the isolated heart model indicate that deleterious effects elicited during I/R directly involves Caspase-1 activation in heart tissue, at least in part, because circulating mediators have been removed. In Applicants' 30-min in situ reperfusion model optimized for preserving cellular function, Applicants observed that Caspase-1 causes dysfunctional glycolytic and mitochondrial flux. Administration of VX-765 prior to reperfusion appeared to rescue glycolytic and mitochondrial function, consistent with the notion that Caspase-1 processes enzymes involve in both metabolic pathways. Degradation of key glycolytic enzymes by Caspase-1 may have impaired recovery during reperfusion and contributed to necrosis during the critical early reperfusion period. Thus, administration of VX-765 prior to reperfusion demonstrated an ability to limit both pyroptotic and necrotic cell death, which are two widely recognize mechanisms that are ultimate culprits in loss of cardiac tissue and ventricular function. VX-765 can serve as an adjunct therapy during reperfusion of patients undergoing an AMI.

This application references various publications. The disclosures of these publications, in their entireties, are hereby incorporated by reference into this application to describe more fully the state of the art to which this application pertains. The references disclosed are also individually and specifically incorporated herein by reference for material contained within them that is discussed in the sentence in which the reference is relied on.

The methodologies and the various embodiments thereof described herein are exemplary. Various other embodiments of the methodologies described herein are possible.

The invention claimed is:

1. A method of treating infarct in a subject in need thereof comprising the steps of:
   administering a $P2Y_{12}$ receptor antagonist, wherein the P2Y12 receptor antagonist is cangrelor;
   administering a cysteine-aspartic protease inhibitor, wherein the cysteine-aspartic protease inhibitor is (S)-1((S)-2-{[1-(4-amino-3-chloro-phenyl)-methanoyl]-amino}-3,3-dimethyl-butanoyl)-pyrrolidine-2-carboxylic acid ((2R,3 S)-2-ethoxy-5-oxo-tetrahydro-furan-3-yl)-amide (VX-765); and
   administering reperfusion therapy.

2. The method of claim 1, wherein the reperfusion therapy comprises percutaneous coronary intervention.

3. The method of claim 1, wherein the reperfusion therapy is administered after administration of cangrelor and VX-765.

4. The method of claim 1, wherein the cangrelor and VX-76 are co-administered.

* * * * *

UNITED STATES PATENT AND TRADEMARK OFFICE
CERTIFICATE OF CORRECTION

PATENT NO. : 11,612,615 B2
APPLICATION NO. : 16/608262
DATED : March 28, 2023
INVENTOR(S) : Jonathon P. Audia et al.

It is certified that error appears in the above-identified patent and that said Letters Patent is hereby corrected as shown below:

In the Specification

Column 1 Line 16 after the Cross-Reference to Related Application, please add the following:
--GOVERNMENT SUPPORT CLAUSE
This invention was made with Government support under grant number R01-HL118334 awarded by the National Institutes of Health. The Government has certain rights in the invention.--

Signed and Sealed this
Twenty-third Day of April, 2024

Katherine Kelly Vidal
*Director of the United States Patent and Trademark Office*